(12) United States Patent
Anderson et al.

(10) Patent No.: US 7,967,817 B2
(45) Date of Patent: *Jun. 28, 2011

(54) MULTI-ELECTRODE LEAD

(75) Inventors: Neil L. Anderson, Roseville (AU); Evan Ka-Loke Chong, South Strathfield (AU)

(73) Assignee: Cathrx Ltd., Eveleigh, New South Wales (AU)

( * ) Notice: Subject to any disclaimer, the term of this patent is extended or adjusted under 35 U.S.C. 154(b) by 362 days.

This patent is subject to a terminal disclaimer.

(21) Appl. No.: 12/173,736

(22) Filed: Jul. 15, 2008

(65) Prior Publication Data

US 2008/0269738 A1 Oct. 30, 2008

Related U.S. Application Data

(62) Division of application No. 10/514,310, filed as application No. PCT/AU03/00560 on May 9, 2003, now Pat. No. 7,415,300.

(30) Foreign Application Priority Data

May 13, 2002 (AU) .......................................... PS2265

(51) Int. Cl.
*A61B 18/14* (2006.01)
*A61B 5/04* (2006.01)
(52) U.S. Cl. .......................................... 606/41; 600/374
(58) Field of Classification Search .................. 600/374, 600/381; 606/41
See application file for complete search history.

(56) References Cited

U.S. PATENT DOCUMENTS

| | | |
|---|---|---|
| 4,101,984 A | 7/1978 | MacGregor |
| 5,109,870 A | 5/1992 | Silny et al. |
| 5,269,810 A | 12/1993 | Hull et al. |
| 5,405,375 A | 4/1995 | Ayers et al. |
| 5,417,208 A | 5/1995 | Winkler |
| 5,522,874 A | 6/1996 | Gates |
| 5,834,051 A | 11/1998 | Woloszko et al. |
| 5,931,862 A | 8/1999 | Carson |

(Continued)

FOREIGN PATENT DOCUMENTS

EP 0 479 435 A2 4/1992

(Continued)

OTHER PUBLICATIONS

European Search Report mailed on Feb. 12, 2007, for EP Application No. 01977995.8 filed on Oct. 19, 2001, five pages.

(Continued)

*Primary Examiner* — Lee S Cohen
(74) *Attorney, Agent, or Firm* — TraskBritt

(57) ABSTRACT

A multi-electrode lead comprises an elongate carrier having a longitudinal axis. A plurality of electrical conductors is carried by the carrier, a plurality of electrodes being connected in spaced relationship to each conductor. The electrodes are arranged at axially spaced intervals along the carrier so that, along the length of the carrier, any one electrode associated with any one of the conductors only once has an electrode associated with another one of the conductors adjacent to that any one electrode. In another aspect of the invention, an ablating device comprises an elongate tubular sleeve for effecting spot ablation of tissue, a sensing electrode catheter being receivable in a passage of a sleeve for assisting in positioning of an ablating electrode, in use. Preferably, the sensing electrode catheter is the multi-electrode lead of the first aspect of the invention.

19 Claims, 2 Drawing Sheets

U.S. PATENT DOCUMENTS

| | | | |
|---|---|---|---|
| 6,071,278 A | 6/2000 | Panescu et al. | |
| 6,088,610 A * | 7/2000 | Littmann et al. | 600/381 |
| 6,120,496 A | 9/2000 | Whayne et al. | |
| 6,144,870 A | 11/2000 | Griffin, III | |
| 6,179,833 B1 | 1/2001 | Taylor | |
| 6,251,107 B1 | 6/2001 | Schaer | |
| 6,325,797 B1 * | 12/2001 | Stewart et al. | 606/41 |
| 6,529,756 B1 * | 3/2003 | Phan et al. | 600/374 |
| 6,771,996 B2 * | 8/2004 | Bowe et al. | 600/374 |
| 7,178,234 B2 | 2/2007 | Kawasaki et al. | |
| 7,415,300 B2 * | 8/2008 | Anderson et al. | 600/374 |
| 2001/0007070 A1 | 7/2001 | Stewart et al. | |

FOREIGN PATENT DOCUMENTS

| | | |
|---|---|---|
| EP | 0 479 435 A3 | 4/1992 |
| WO | WO-90/08466 A1 | 8/1990 |
| WO | WO-96/36860 A2 | 11/1996 |
| WO | WO-96/36860 A3 | 11/1996 |

OTHER PUBLICATIONS

International Search Report mailed on Jul. 1, 2003, for PCT Application No. PCT/AU03/00560 filed on May 9, 2003, 6 pages.

* cited by examiner

MULTI-ELECTRODE LEAD

CROSS-REFERENCE TO RELATED APPLICATIONS

This application is a divisional of U.S. application Ser. No. 10/514,310, filed Aug. 25, 2005, now U.S. Pat. No. 7,415,300, issued Aug. 19, 2008, which is a National Phase filing under 35 U.S.C. §371 of International Application No. PCT/AU03/00560, filed May 9, 2003, the contents of each of which are incorporated herein by reference in their entirety.

FIELD

This invention relates to a multi-electrode lead. More particularly, the invention relates to a multi-electrode lead for use in medical applications for sensing predetermined parameters, such as, for example, electrical activity, temperature, or the like.

BACKGROUND

Electrodes are used in the medical field for applications such as stimulation, sensing, ablation and defibrillation.

Typically, such a lead is in the form of a catheter, which is inserted through a blood vessel of a patient's body to the desired location in the patient's body.

The thinner the electrical lead, the easier it is to insert and manipulate. Further, by making the lead thinner, the patient suffers less discomfort.

SUMMARY

According to a first aspect of the invention, there is provided a multi-electrode lead that comprises:

an elongate carrier having a longitudinal axis; and a plurality of electrical conductors carried by the carrier, a plurality of electrodes being connected in spaced relationship to each conductor, the electrodes being arranged at axially spaced intervals along the carrier so that, along the length of the carrier, any one electrode associated with any one of the conductors only once has an electrode associated with another one of the conductors adjacent to the any one electrode.

In this specification, unless the context clearly indicates otherwise, the term "adjacent" is to be understood to mean that one electrode is next to, but spaced from, its neighboring electrode.

In a preferred embodiment of the invention, the carrier comprises a mandrel about which the conductors are carried, for example, by being helically wound around the mandrel.

The mandrel is, preferably, a tubular mandrel to form a lumen of the lead. The mandrel may be a flexible plastic tube.

A covering of a non-conductive material may be applied about the conductors to cover the conductors.

The electrodes may be formed by elements of electrically conductive material applied to an outer surface of the covering. The material from which the elements are made may be a biocompatible metal such as, for example, platinum.

Each element may be in the form of a band or annulus arranged about the carrier. A first of the electrodes may be arranged at a distal end of the carrier.

In one embodiment of the invention, at least at that region of the carrier having the electrodes, the covering may be of a porous material. Where the coating is of a porous material, metal may be applied about the coating to permeate through the pores of the coating to make contact with the conductors.

Instead, in another embodiment of the invention, the coating may be removed at regions where it is desired to form electrodes to expose conductors at that region with the metal forming the elements being in direct electrical contact with their associated conductors.

In yet another embodiment of the invention, each electrode may be defined by a region of a conductor exposed by the removal of the covering at that region, with or without a conductive element applied to the exposed region.

According to a second aspect of the invention, there is provided an ablating device, the ablating device comprising:

an elongate, tubular sleeve defining an open passage; and an ablating electrode carried at a distal end of the sleeve for effecting spot ablation of tissue, a sensing electrode catheter being receivable in the passage of the sleeve for assisting in positioning of the ablating electrode, in use.

In a preferred form of the invention, the ablating device is used in combination with the multi-electrode lead as described above where, by positioning the sleeve over the electrodes of the lead, appropriate positioning of the ablating electrode of the ablating device can be achieved. It will be appreciated that, as the ablating device passes over and covers the electrodes of the multi-electrode lead, the signals from the covered electrodes become attenuated. As a result, a clinician is able to monitor the progress of the ablating device relative to the lead. Therefore, the sensing electrode catheter may be the multi-electrode lead as described above.

Accordingly, a third aspect of the invention provides an ablating assembly that includes, in combination, a multi-electrode lead, as described above; and an ablating device, also as described above.

According to a fourth aspect of the invention, there is provided a method of monitoring a predetermined parameter in a patient, the method comprising the steps of:

inserting a multi-electrode lead, as described above, through a body vessel of the patient;

placing the electrodes of the multi-electrode lead at a desired site in the patient;

monitoring the parameter at least certain of the electrodes; and processing signals received from the electrodes for determining a value of the parameter.

Where the parameter being monitored is abnormal electrical activity, the method may include processing the signals by, in respect of each conductor, summing the signals received from the electrodes connected to that conductor, at least one of the received signals being representative of normal electrical activity. The method may then include determining a time delay resulting from spatial separation of the electrodes of that conductor. Still further, the method may include subtracting the signals that reflect normal electrical activity.

Where the parameter being monitored is temperature, the method may include monitoring the temperature at the site using a first electrode of the lead that is arranged closest to the site. The method may then include also monitoring the temperature at a position remote from the site by using a second electrode to give a reference, body temperature. Still further, the method may include subtracting the temperature monitored by the second electrode from the temperature monitored by the first electrode to give an indication of the temperature at the site.

BRIEF DESCRIPTION OF THE DRAWINGS

The invention is now described, by way of example, with reference to the accompanying drawings in which.

DETAILED DESCRIPTION

Figure 1:
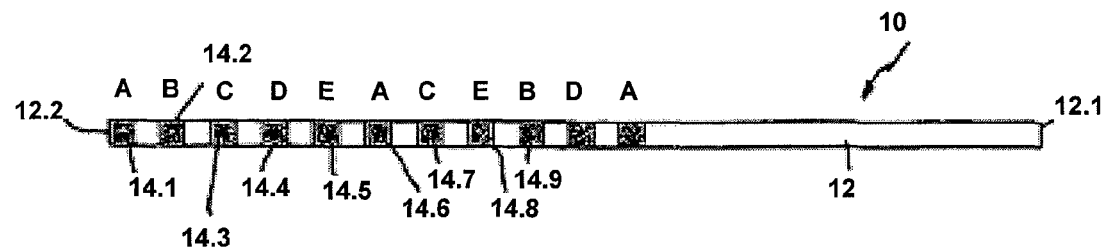
FIG. 1 shows a side view of a multi-electrode lead in accordance with a first aspect of the invention.

Referring initially to FIG. 1 of the drawings, a multi-electrode lead in the form of a catheter 10, in accordance with a first aspect of the invention, is illustrated and is designated generally by the reference numeral 10. The catheter 10 includes an elongate, tubular carrier 12 having a proximal end 12.1 and a distal end 12.2 and defining a longitudinal axis.

A plurality of electrodes 14 is arranged at axially spaced intervals about an outer periphery of the carrier 12, proximate the distal end 12.2 of the tubular carrier 12.

Figure 3:
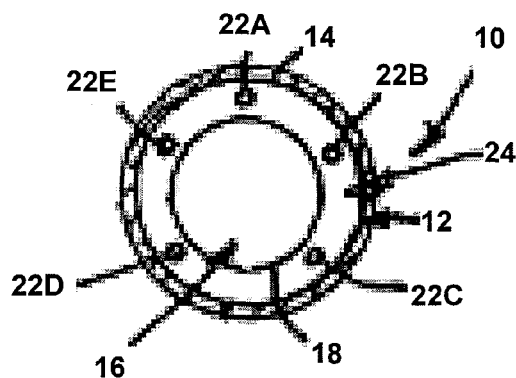
FIG. 3 shows a schematic sectional end view of a multi-electrode lead.

The carrier 12 supports a plurality of conductors. Although not shown in FIG. 1 of the drawings, a cross-sectional view of the catheter 10 is shown in FIG. 3 of the drawings. The catheter 10 has the tubular carrier 12 defining a lumen 16. The electrodes 14, as described above, are carried about an outer periphery of the tubular carrier 12. In the formation of the catheter 10, an inner, tubular mandrel 18 is provided. A plurality of conductors 22 are arranged about the mandrel 18 and a layer or coating 24 of an electrically insulating material is applied about the mandrel 18 with the conductors 22 being embedded in the layer 24.

Each electrode 14 is electrically connected to one of the conductors 22. Each conductor 22 has more than one electrode 14 connected to it at axially spaced intervals along the length of the carrier 12.

To connect one of the electrodes 14 to its associated conductor 22, the material 24 at the relevant location of the carrier 12 is removed to expose the conductor 22. When the metal used to form the electrode 14 is applied by appropriate deposition techniques, the metal is brought into electrical contact with the relevant conductor 22 to connect the electrode 14 to that conductor 22. As illustrated in FIG. 3 of the drawings, the electrodes 14 are annular or band-shaped and extend about an outer circumference of the carrier 12.

Figure 2:
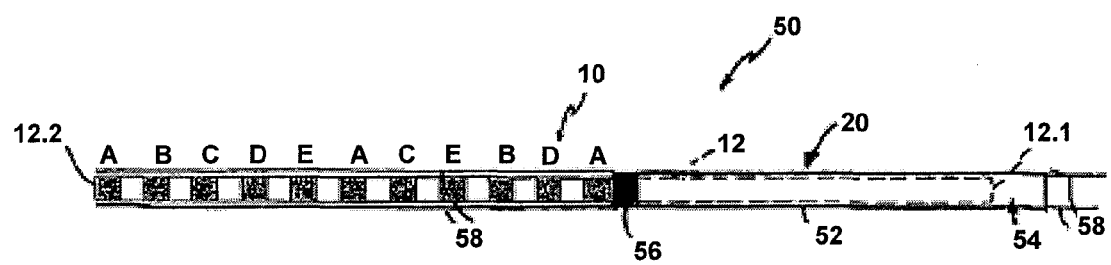
FIG. 2 shows a schematic side view of an ablating assembly in accordance with a third aspect of the invention, the ablating assembly including an ablating device in accordance with a second aspect of the invention.

As described above, each conductor 22 has more than one electrode 14 connected to it. In the example illustrated, the catheter 10 contains five conductors 22. One of the conductors 22A has three electrodes 14 associated with it as illustrated in FIGS. 1 and 2 of the drawings, while each of the remaining conductors 22B-22E, has two electrodes 14 associated with it.

The electrodes 14 are arranged along the carrier 12 such that any one electrode 14 associated with any one of the conductors 22 only once has an electrode 14 associated with another one of the conductors 22 adjacent to it. For example, as illustrated in FIG. 1 of the drawings, electrode 14.1 is connected to conductor 22A.

Electrode 14.2 is connected to conductor 22B, electrode 14.3 is connected to conductor 22C, electrode 14.4 is connected to conductor 22D and electrode 14.5 is connected to conductor 22E. The following electrode, electrode 14.6, is then, again, connected to conductor 22A and the next electrode 14.7 is connected to conductor 22C and so on. The benefit of this arrangement is that a large number of electrodes, in this case, eleven electrodes, can be arranged on the catheter 10 but with the catheter 10 having fewer conductors 22. This makes the catheter 10 of smaller diameter than would otherwise be the case, making it more easily maneuverable within blood vessels of the patient. The patient's body can act as the return electrode for each of the electrodes 14.

The catheter 10 is used for sensing one of a number of parameters of a patient's body. For example, the catheter 10 can be used in sensing abnormal electrical activity in the heart or brain of a patient. For monitoring cardiac activity, this is achieved by inserting the catheter 10 via a patient's femoral vein to the desired location in the patient's heart. The electrodes 14 of the catheter 10 are used for monitoring or sensing electrical activity in pulmonary veins of the patient. The electrical activity is sensed by the electrodes 14 and return signals are sent from the electrodes 14 to a control device (not shown). The return signal from each electrode 14 is monitored to decide which electrode 14 is sensing the highest level of abnormal electrical activity. If, for example, the signals on conductors 22B and 22C carry the signals indicating abnormal electrical activity that would be an indication that the abnormal electrical activity took place at, or between, electrodes 14.2 and 14.3. By appropriate signal processing, it can be determined at which electrode 14 the highest level of abnormal electrical activity occurred.

Figure 4:
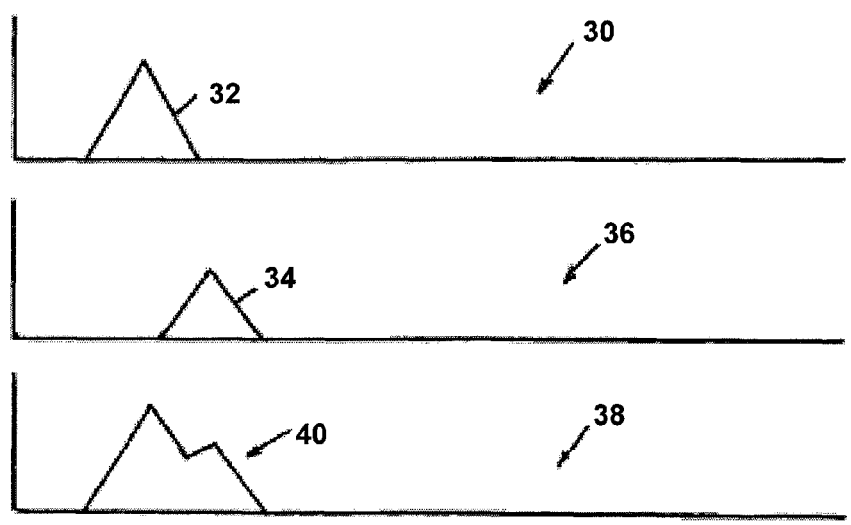
FIG. 4 shows a set of graphs indicating, in a simplified manner, the operation of the multi-electrode lead of FIG. 1.

Referring to FIG. 4, and with continured reference to FIG. 1, of the drawings, a simplified version of the manner of determining where the highest level of abnormal electrical activity occurred is shown. For example, in graph 30, a pulse 32 is detected by electrode 14.2 and is conveyed along conductor 22B to the control unit. A further pulse 34 would be monitored by electrode 14.9, which is also connected to conductor 22B, as shown in graph 36. This pulse 34 is temporally spaced with respect to pulse 32. What is received at the control box on conductor 22B is, as shown in graph 38, a pulse 40, which is the sum of the pulses 32 and 34. The control box can determine, due to the smaller amplitude of the pulse 34, that it represents normal electrical activity. By filtering out or subtracting this pulse 34, the pulse 32 remains, which is representative of abnormal electrical activity at electrode 14.2. Appropriate remedial action can then be taken.

Referring now to FIG. 2 of the drawings, an ablating assembly, in accordance with a third aspect of the invention, is illustrated and is designated generally by the reference numeral 50. This ablating assembly 50 incorporates the catheter 10 as described above with reference to FIG. 1 of the drawings. An ablating device 20, in accordance with a second aspect of the invention, comprising a sleeve 52 is received over the lead 10. The sleeve 52 has a passage 54 of sufficiently large diameter to accommodate the catheter 10. An ablating electrode 56 is arranged at a distal end of the sleeve 52 and a pulley arrangement, using wires 58, is used to position the sleeve 52 relative to the catheter 10.

Using the example described above, assuming the abnormal electrical activity is determined as having occurred at or adjacent electrode 14.2, then, while the catheter 10 remains in situ, the catheter 10 is received in the passage 54 of the ablating sleeve 52. The sleeve 52 is maneuvered along the catheter 10 so that the ablating electrode 56 overlies the electrode 14.2. An ablating pulse is sent down the sleeve 52 to ablate tissue adjacent the electrode 14.2 to create a lesion. The lesion inhibits the continued abnormal electrical activity at that site.

When the catheter 10 is used for measuring temperature, the arrangement is slightly different in that, unlike when electrical activity is being sensed, a return lead is required. Accordingly, a return wire (not shown) for a thermocouple is included. This return wire is also embedded in the layer 24 of the carrier 12 (FIG. 3).

In sensing temperature, if ablation is to occur at or adjacent the electrode 14.2, then, using the ablating electrode 56 of the ablating assembly 50, the temperature at that electrode 14.2 is monitored together with the temperature of another electrode remote from electrode 14.2, for example, electrode 14.9. The temperatures of the monitored electrodes 14.2 and 14.9 are summed. It is reasonable to assume that the temperature at electrode 14.9, because it is remote from the ablation site, is at body temperature. Therefore, when the temperature monitored by the electrode 14.9 is subtracted from the summed temperatures of electrodes 14.2 and 14.9, the remaining temperature is an indication of the temperature at electrode 14.2. This temperature can be monitored to inhibit overheating of the site.

Referring again to FIG. 3 of the drawings, a benefit of having the conductors 22 embedded in the layer 24 is that the lumen 16 of the tubular carrier 12 is free to allow other pieces of equipment (not shown), for example, a steering mechanism, a lasso, a conduit for a cooling solution, or the like, to pass through the lumen 16.

Accordingly, it is an advantage of the invention that a multi-electrode lead, or catheter, is provided, which is far thinner than other multi-electrode leads of which the applicant is aware. Also, the multi-electrode lead can be used for sensing various different parameters of the patient's body such as electrical activity, temperature, or the like. Due to the fact that the lumen of the lead or catheter is unobstructed by conductors, the lumen can be used for other purposes such as a steering mechanism, a shape forming member, the introduction of a cooling solution, or the like.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An ablating device, the ablating device comprising:
   an elongate, tubular sleeve defining an open passage; and
   an ablating electrode carried at a distal end of the sleeve for effecting spot ablation of tissue, a sensing electrode catheter being receivable in the open passage of the sleeve for assisting in positioning of the ablating electrode, in use; and
   a sensing electrode catheter received in the open passage of the sleeve, the sensing electrode catheter being in the form of a multi-electrode lead comprising:
      an elongate carrier having a longitudinal axis; and
      a plurality of electrical conductors carried by the carrier, a plurality of electrodes being connected in spaced relationship to each conductor, the plurality of electrodes being arranged at axially spaced intervals along the carrier so that, along the length of the carrier, any one electrode associated with any one of the conductors only once has an electrode associated with another one of the conductors adjacent to the any one electrode.

2. The ablating device of claim 1 in which the carrier comprises a mandrel about which the conductors are carried.

3. The ablating device of claim 2 in which the mandrel is a tubular mandrel to form a lumen of the lead.

4. The ablating device of claim 1 in which a covering of a non-conductive material is applied about the plurality of electrical conductors to cover the plurality of electrical conductors.

5. The ablating device of claim 4 in which the plurality of electrodes is formed by elements of electrically conductive material applied to an outer surface of the covering.

6. The ablating device of claim 5 in which the electrically conductive material from which the elements are made is a biocompatible metal.

7. The ablating device of claim 6 in which each element is in the form of a band or annulus arranged about the carrier.

8. The ablating device of claim 7 in which, at least at a region of the carrier having the plurality of electrodes, the covering is of a porous material.

9. The ablating device of claim 8 in which, where the covering is of a porous material, a metal is applied about the covering to permeate through the pores of the covering to make contact with the plurality of electrical conductors.

10. The ablating device of claim 6 in which the covering is removed at regions where it is desired to form electrodes to expose the plurality of electrical conductors at a region with the metal forming the elements being in direct electrical contact with their associated conductors.

11. The ablating device of claim 10 in which each electrode is defined by a region of each conductor exposed by the removal of the covering at that region.

12. The ablating device of claim 1 in which the ablating electrode is a ring electrode arranged at the distal end of the sleeve.

13. A method of ablating tissue at a site in a patient's body, the method comprising:
   inserting an ablating device, as claimed in claim 1, through a body vessel of the patient;
   placing the electrodes of the multi-electrode lead in a desired position at the site in the patient;
   monitoring predetermined parameters at least certain of the electrodes;
   processing signals received from the electrodes for determining a value of the parameter; and
   positioning the ablating electrode of the sleeve over a selected electrode of the multi-electrode lead and effecting ablation at the site using the ablating electrode.

14. The method of claim 13, which includes where the parameter being monitored is abnormal electrical activity, processing the signals by, in respect of each conductor, summing the signals received from the electrodes connected to that conductor, at least one of the received signals being representative of normal electrical activity.

15. The method of claim 14, which includes determining a time delay resulting from spatial separation of the electrodes of that conductor.

16. The method of claim 15, which includes subtracting the signals which reflect normal electrical activity.

17. The method of claim 13, which includes where the parameter being monitored is temperature, monitoring the temperature at the site using a first electrode of the lead, which is arranged closest to the site.

18. The method of claim 17, which includes also monitoring the temperature at a position remote from the site by using a second electrode to give a reference, body temperature.

19. The method of claim 18, which includes subtracting the temperature monitored by the second electrode from the temperature monitored by the first electrode to give an indication of the temperature at the site and to inhibit overheating of the site by the ablating electrode.

* * * * *

UNITED STATES PATENT AND TRADEMARK OFFICE
CERTIFICATE OF CORRECTION

PATENT NO. : 7,967,817 B2  
APPLICATION NO. : 12/173736  
DATED : June 28, 2011  
INVENTOR(S) : Neil L. Anderson and Evan Ka-Loke Chong Page 1 of 1

It is certified that error appears in the above-identified patent and that said Letters Patent is hereby corrected as shown below:

On the title page:
In ITEM (73) Assignee:   change "Cathrx Ltd.," to --CathRx Ltd.,--

In the specification:
COLUMN 2, LINE 38, change "parameter at least" to --parameter at at least--
COLUMN 3, LINE 50, change "22B-22E, has" to --22B-22E has--
COLUMN 4, LINES 54,55 change "remains in situ," to --remains *in situ*,--

In the claims:
CLAIM 13, COLUMN 6, LINE 33, change "parameters at least" to --parameters at at least--

Signed and Sealed this
Twenty-second Day of November, 2011

David J. Kappos
*Director of the United States Patent and Trademark Office*